US009715962B2

(12) United States Patent
Beyerlein et al.

(10) Patent No.: US 9,715,962 B2
(45) Date of Patent: Jul. 25, 2017

(54) CONTROLLING A CONTACTLESS ENERGY TRANSMISSION BY MEANS OF A CHARACTERISTIC OF A RESONANT CIRCUIT

(75) Inventors: Walter Beyerlein, Bubenreuth (DE); Stefan Henke, Erlangen (DE); Florian Hofmann, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 838 days.

(21) Appl. No.: 14/124,684

(22) PCT Filed: May 21, 2012

(86) PCT No.: PCT/EP2012/059387
§ 371 (c)(1),
(2), (4) Date: Dec. 6, 2013

(87) PCT Pub. No.: WO2012/168056
PCT Pub. Date: Dec. 13, 2012

(65) Prior Publication Data
US 2014/0097699 A1     Apr. 10, 2014

(30) Foreign Application Priority Data

Jun. 7, 2011 (DE) .......................... 10 2011 077 085

(51) Int. Cl.
*H02M 3/335* (2006.01)
*H02J 5/00* (2016.01)
(Continued)

(52) U.S. Cl.
CPC .............. *H01F 38/14* (2013.01); *A61B 6/56* (2013.01); *H02J 5/005* (2013.01); *H02M 3/33523* (2013.01); *Y02B 70/1433* (2013.01)

(58) Field of Classification Search
CPC ..... H01F 38/14; H02M 3/33523; H02J 5/005; A61B 6/56; Y02B 70/1433
(Continued)

(56) References Cited

U.S. PATENT DOCUMENTS 5,608,771 A * 3/1997 Steigerwald ............. A61B 6/56
378/15
6,344,979 B1 * 2/2002 Huang .................. H02M 3/337
363/131
(Continued)

FOREIGN PATENT DOCUMENTS

CN          1368787 A       9/2002
DE     102005020186 A1     11/2006
(Continued)

OTHER PUBLICATIONS

Chinese Office Action for Chinese Application No. 201280027733.3, mailed Jun. 25, 2015 with English Translation.
(Continued)

*Primary Examiner* — Jared Fureman
*Assistant Examiner* — Michael Warmflash
(74) *Attorney, Agent, or Firm* — Lempia Summerfield Katz LLC

(57) ABSTRACT

The embodiments relate to a circuit for transmitting an input voltage from an electrical energy source in a stator to a load within a device movable relative to the stator including an control element for converting an input voltage into a transmission voltage, a resonant circuit for receiving the transmission voltage, wherein the resonant circuit contains a capacitor and a primary winding of a transformer and the transformer having the primary winding and a secondary winding, wherein the primary winding is provided for transmitting the transmission voltage to the secondary winding
(Continued)

and the secondary winding is provided for supplying the received transmission voltage to the load.

28 Claims, 3 Drawing Sheets

(51) Int. Cl.
    *H01F 38/14*     (2006.01)
    *A61B 6/00*     (2006.01)

(58) Field of Classification Search
    USPC ........................................................ 307/104
    See application file for complete search history.

(56) References Cited

U.S. PATENT DOCUMENTS

| | | | | |
|---|---|---|---|---|
| 6,351,626 B1* | 2/2002 | Lohr | ...................... | H01F 38/14 324/207.25 |
| 7,054,411 B2* | 5/2006 | Katcha | .................... | H05G 1/10 336/105 |
| 7,899,150 B2* | 3/2011 | Beyerlein | ................ | A61B 6/56 378/101 |
| 8,004,235 B2* | 8/2011 | Baarman | ............... | H02J 7/0072 320/108 |
| 8,129,865 B2* | 3/2012 | Krumme | .................. | A61B 6/56 307/104 |
| 2007/0222426 A1* | 9/2007 | Waffenschmidt | ....... | H01F 38/14 323/355 |
| 2008/0079392 A1 | 4/2008 | Baarman et al. | | |

FOREIGN PATENT DOCUMENTS

| | | |
|---|---|---|
| DE | 102007006394 A1 | 5/2008 |
| WO | 9832217 | 7/1998 |

OTHER PUBLICATIONS

German Office Action dated May 10, 2012 in corresponding German Patent Application No. DE 10 2011 077 .85.2 with English translation.
International Search Report and Written Opinion in PCT/EP2012/059387 dated Nov. 26, 2012, with English translation.

* cited by examiner

CONTROLLING A CONTACTLESS ENERGY TRANSMISSION BY MEANS OF A CHARACTERISTIC OF A RESONANT CIRCUIT

The present patent document is a §371 nationalization of PCT Application Serial Number PCT/EP2011/059387, filed May 21, 2012, designating the United States, which is hereby incorporated by reference, and this patent document also claims the benefit of DE 10 2011 077 085.2, filed Jun. 7, 2011, which is also hereby incorporated by reference.

TECHNICAL FIELD

The embodiments relate to a circuit, a tomograph, particularly a computer tomograph, and to a method.

BACKGROUND

In many electrical appliances, there is a device that is movable with respect to a stator and is supplied with energy from an energy source via the stator. An example of this is a tomograph such as, for example, a computer tomograph, having an annular tunnel in which an object may be accommodated, the structure of which is to be recorded. The annular tunnel is also called a gantry in conjunction with a computer tomograph. In the annular tunnel, a number of imaging sensors are arranged that move around the object with the annular tunnel and thus scan the object. From the sum of all scanned values, an image of the structure of the object is generated that may be output, for example, on a screen.

To supply the imaging sensors and other elements in the annular tunnel, such as, for example, an X-ray source or a data transmission device for transmitting the scanned values to a processor in the stator, with electrical energy and in order to send the data to the stator, various methods are known conventionally. On the one hand, the electrical energy and the data may be transmitted to the annular tunnel via a cable that, however, restricts the margin for movement due to the finite length of the cable. On the other hand, it is known to use sliding contacts that slide at the annular tunnel or at the stator that, however, leads not only to a high material wear but also entails a high requirement of space. Finally, it is known to transmit the electrical energy inductively that, however, leads to a poor efficiency of the transmission due to high losses due to parasitic elements such as the stray inductance of the magnetic coupling. To lower the losses, U.S. Pat. No. 5,608,771 proposes to attenuate the stray inductance by a capacitance connected in series with the stray inductance.

In every case, it is necessary to stabilize the load voltage in the annular tunnel.

It is an object of the embodiments to improve the stabilization of the load voltage in a device movable relative to a stator.

SUMMARY AND DESCRIPTION

The scope of the claimed invention is defined solely by the appended claims and is not affected to any degree by the statements within this summary. The present embodiments may obviate one or more of the drawbacks or limitations in the related art.

The embodiments are based on the concept of improving the stabilization of the load voltage by a control of the load voltage. The embodiments are based on the finding that the load voltage is conventionally stabilized by controlling the input voltage at the stator on the basis of a feedback of the load voltage from the annular tunnel. It is a further finding of the embodiments that at the beginning of an electrical energy transmission by magnetic coupling, the possibilities for wireless feedback of the load voltage are limited because a corresponding data transmission device is first supplied with electrical energy. When using magnetic coupling, as a result, it may take a very long time in some cases until the feedback for the control is available. When the feedback is finally available, the load voltage may be changed into states from which, after an intervention of the control, it takes a very long time to stabilize the load voltage. However, a transformer operating by magnetic coupling may be divided, in network theory, into a transformer without losses, into a main inductance connected in parallel with the transformer on the input side, and into a stray inductance connected in series on the input side. If a capacitance is connected to the input of the transformer, the resonant circuit produced therefore acts only at the input side and dominates the transmission characteristic of the entire system. If the transmission characteristic and the input voltage of the transformer are known, the load voltage may be derived without having to be measured. The conventional control of the load voltage may therefore be omitted at least in the initial phase and replaced by simple control. This is particularly advantageous for the electrical energy transmission by magnetic coupling since the load voltage itself may be stabilized even without a data transmission device in the start-up phase of the entire system.

The embodiments, therefore, specify a circuit for transmitting an input voltage from an electrical energy source in a stator to a load within a device movable relative to the stator, which includes the following features: an actuating element for converting an input voltage into a transmission voltage, a resonant circuit for receiving the transmission voltage, wherein the resonant circuit contains a capacitance and a primary winding of a transformer; and the transformer including the primary winding and a secondary winding, wherein the primary winding is provided for transmitting the transmission voltage to the secondary winding and the secondary winding is provided for delivering the received transmission voltage to the load, wherein the actuating element is provided for adjusting the frequency of the transmission voltage in such a manner that the transmission ratio of the resonant circuit remains constant for a predetermined range of values of a load that may be connected to the secondary winding so that the transmission ratio of the resonant circuit is independent of the load within the predetermined range of values.

The embodiments have the advantage that the stray inductance of the transformer may now be applied usefully for stabilizing the load voltage. Due to the load-independent transmission ratio, the circuit requires, in particular, no feedback from the movable device so that a control of the load voltage may be omitted. This reduces the complexity of the overall system and renders the system more insusceptible to faults.

In a particular embodiment, the actuating element may be provided for adjusting the frequency of the transmission voltage on the basis of a control characteristic in which the transmission characteristic of the resonant circuit is plotted over the frequency to be adjusted.

In an embodiment, a shape of the control characteristic may remain constant within the predetermined range of values of the load so that the shape of the control characteristic is independent of the load within the predetermined range of values.

In an embodiment, the actuating element is provided for adjusting the frequency within a predetermined frequency range. This enables the technical limits to be taken into consideration in the detection, processing and provision of the control characteristic and avoids the operation of a system having the specified circuit in unknown operating states damaging the system.

In an embodiment, the capacitance is selected in such a manner that the resonant frequency of the electrical resonant circuit is outside the predetermined frequency range. In this manner, a strictly monotonous control characteristic is provided. This enables a control system to intervene in the control at any time. Without the strict monotony of the control characteristic, the control system may intervene at a point of the control characteristic that the control system moves away from the operating point to be corrected in the control characteristic and thus runs unstably. This risk is avoided effectively by removing the resonant frequency from the frequency range.

In an embodiment, the frequency range is selected in such a manner that the control characteristic has a fixed frequency in which the transmission ratio of the resonant circuit is independent of an impedance of the load. Within the range of this fixed frequency in the control characteristic, reliable controllability of the load voltage is given even when the load impedance is to be increased from a rest state and its load states thus change continuously.

In an additional embodiment, the fixed frequency is the limit frequency of the frequency range that is on the side of the frequency range directed toward the resonant frequency. This avoids the resonant frequency falling into the frequency range due to changes of the load state at the load impedance. This may happen because the control characteristic of the resonant circuit becomes deformed with increasing load and the resonant frequency during this process approaches the fixed frequency more and more. Although the resonant frequency may approach the frequency range arbitrarily, for example during the starting-up of the load impedance described before, due to the position of the frequency range according to the additional development, the resonant frequency may never fall into the frequency range.

In another embodiment, the other limit frequency of the frequency range is allocated to a transmission ratio of the resonant circuit, the change of which is limited to a predetermined value for a predetermined range of load states of the load impedance. In this manner, further stabilization of the control characteristic is achieved for a particular operating state.

The predetermined range of load states may include the load states during start-up of a load, connected to the circuit, in the movable device. Thus, the load may be started up with a constant supply voltage in the movable device on switch-on so that a load-independent control characteristic is achieved for the large load impedances present on start-up of the load and thus for low loads.

In another embodiment, the actuating element is provided for calling up the control characteristic from a memory so that the control characteristic is immediately available and does not have to be first acquired anew by calculation, measurement or other ways when the circuit is started.

In an embodiment, the circuit has a write device for storing values of the control characteristic in the memory on the basis of a measurement of the transmission ratio of the resonant circuit. In this manner, the control characteristic may be configured to the real transmission characteristic of the resonant circuit when, for example, the values of the individual components of the resonant circuit change with time.

In an embodiment, the write device is provided for measuring the transmission ratio on the basis of a sweep of the frequency of the transmission voltage. A sweep is a sinusoidal signal, the frequency of which changes continuously starting from a lower limit frequency to an upper limit frequency. Such a sweep may be generated simply by a frequency generator and enables the control characteristic to be recorded with an arbitrarily high accuracy.

In an embodiment, the circuit is provided for directly connecting the resonant circuit to an output of the circuit during the sweep since, as a rule, movement of the movable device is not necessary during the learning process.

In another embodiment, the write device is provided for measuring the transmission ratio on the basis of a voltage pulse as transmission voltage, the write device being provided for detecting a resonant circuit current with which the resonant circuit reacts as response to the voltage pulse. The voltage pulse may be implemented not only with comparatively little energy but the measurement may also be performed within a comparatively short period of time. Nevertheless, the phase difference between the voltage pulse and the resonant circuit current contains all the necessary information for determining the transmission ratio. Due to the shortness of the voltage pulse, the measuring of the transmission ratio of the resonant circuit based on the voltage pulse may also be performed during the operation of the load in order to update the control characteristic continuously.

In another embodiment, the circuit has a current measuring device for measuring a resonant circuit current through the resonant circuit, wherein the actuating element is provided for controlling the frequency of the transmission voltage in such a manner that the resonant circuit current does not exceed a predetermined value. This provides that the current through the resonant circuit remains limited in order to protect the individual components in the circuit against an electrical overload.

In a further embodiment, the circuit has a voltage measuring device for measuring the load voltage, wherein the actuating element is provided for controlling the load voltage on the basis of the frequency of the transmission voltage in such a manner that the load voltage follows a nominal voltage value. In this manner, the accuracy of the load voltage may be increased further in order to correct, for example, unexpected disturbances for the load voltage.

In an embodiment, the voltage measuring device is arranged on the stator side in the circuit, the voltage measuring device having a data receiving device for receiving the load voltage from the movable device. These data receiving devices may utilize in a particularly advantageous manner a pre-established data link of the movable device for the transmission of measurement data or other useful data in order to receive the load voltage. The control system for the load voltage may thus be implemented in a space-saving and cost-effective manner in the circuit.

In another embodiment, the circuit is provided for starting the control of the load voltage on the basis of the frequency when the load voltage is available at the data receiving device. In this manner, the load voltage is initially converted by the actuating element, during the control process, into a state close to the state to be corrected so that the control of the load voltage may adjust the state quickly and stably to the state to be corrected. Furthermore, the control characteristic may also be used during the control of the load voltage for including the input voltage as interference variable intrusion into the control of the load voltage.

In a further development, the circuit is provided for ending the adjustment of the frequency of the transmission voltage on the basis of the control characteristic and thus the control of the load voltage when the control of the load voltage has been started. In this manner, it is possible to avoid the dynamic range of the control loop being restricted by the control of the load voltage.

In another embodiment, the transformer has an additional inductance connected in series with the primary winding so that the stray inductance may be increased, if necessary, when the capacitance is insufficient for achieving a desired transmission characteristic for the resonant circuit. Even if capacitors having suitable capacitances were available in theory, capacitors having capacitances that are more cost effective, more space-saving or more failure-proof may also be used for dimensioning the transmission characteristic of the resonant circuit due to the additional inductance. The margin for dimensioning of the resonant circuit is therefore extended by the additional inductance.

In a development of the circuit specified, the capacitance, the additional inductance and the primary winding are connected in series so that an LLC converter is obtained that is available as a standard circuit so that the resonant circuit may be implemented cost-effectively. An LLC converter is an electrical component of a transformer, to the input of which a capacitor and a coil are connected in series.

In an additional embodiment, the circuit includes a further resonant circuit symmetric to the resonant circuit, which has a series circuit of a symmetry capacitance corresponding to the capacitance and a symmetry inductance corresponding to the additional inductance, wherein the primary winding is connected between the resonant circuit and the symmetry resonant circuit. Since the two resonant circuits are correspondingly located at the feed line to and the bleed line from the primary winding, the two resonant circuits receive the transmission voltage displaced by one half wave. This has the effect that interfering emissions generated by the resonant circuits are also radiated displaced by one half wave so that the two resonant circuits cancel each other.

In another embodiment, the capacitance is connected in series with the primary winding, the circuit having a relief capacitance that is connected in parallel with the primary winding. The relief capacitance may be optimized for short-circuiting highly transient components in the transmission voltage and thus filtering the transient components out of the transmission voltage. Optimizing the relief capacitance limits the rise of the transmission voltage and the radiation of interfering emissions by the resonant circuit is reduced further.

The embodiments also specify a tomograph, particularly a computer tomograph, for recording the spatial structure of an object arranged in an annular tunnel, wherein the annular tunnel rotates around a stator during the recording. The tomograph includes a circuit transmitting an input voltage from an electrical energy source to a load within the annular tunnel.

Also, an embodiment is a method for transmitting an input voltage from an electrical energy source in a stator to a load within a device movable relative to the stator having the acts of converting an input voltage into a transmission voltage, receiving the transmission voltage with a resonant circuit that contains a capacitance and a primary winding of a transformer, transmitting the transmission voltage to a secondary winding of the resonant circuit, delivering the transmission voltage received by the secondary winding to the load, detecting the input voltage and adjusting the frequency of the transmission voltage on the basis of a control characteristic in such a manner that the amplitude of the load voltage dropped across the load remains constant, the transmission ratio of the resonant circuit being plotted over the frequency to be adjusted in the control characteristic.

Developments of the method may be method acts that implement the features of the specified circuit.

BRIEF DESCRIPTION OF THE DRAWINGS

The characteristics, features and advantages, described above, and the manner in which these are achieved will become clearer and more clearly comprehensible in conjunction with the following description of the exemplary embodiments that are explained in greater detail in conjunction with the drawings, in which.

DETAILED DESCRIPTION

The exemplary embodiments described in the text that follows may be combined with one another also in parts.

Figure 1:
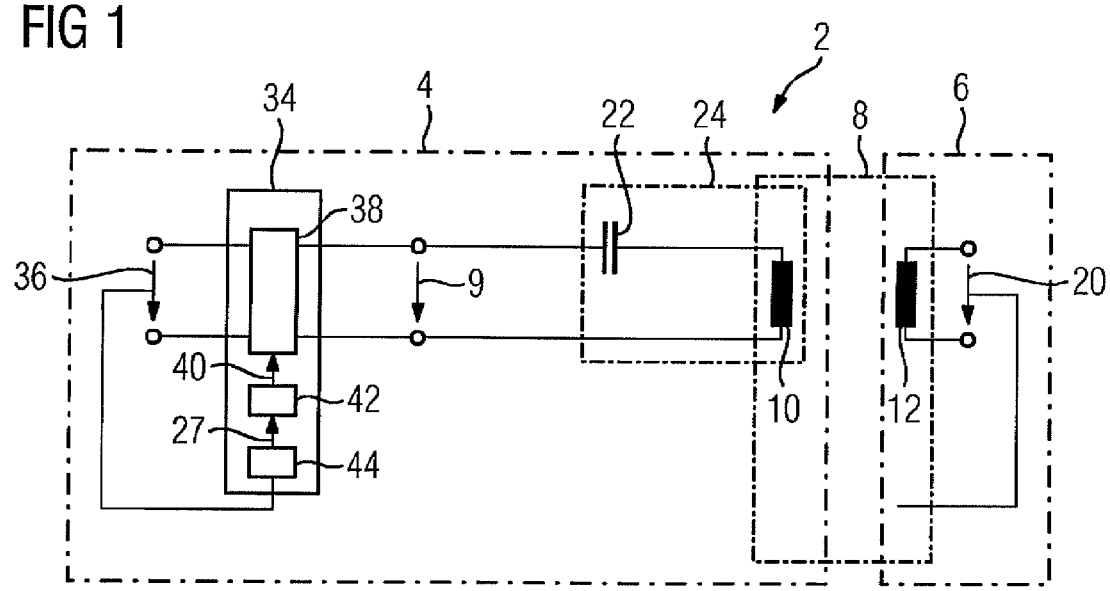
FIG. 1 depicts a circuit diagram of a first exemplary embodiment of the specified circuit.
Figure 3:
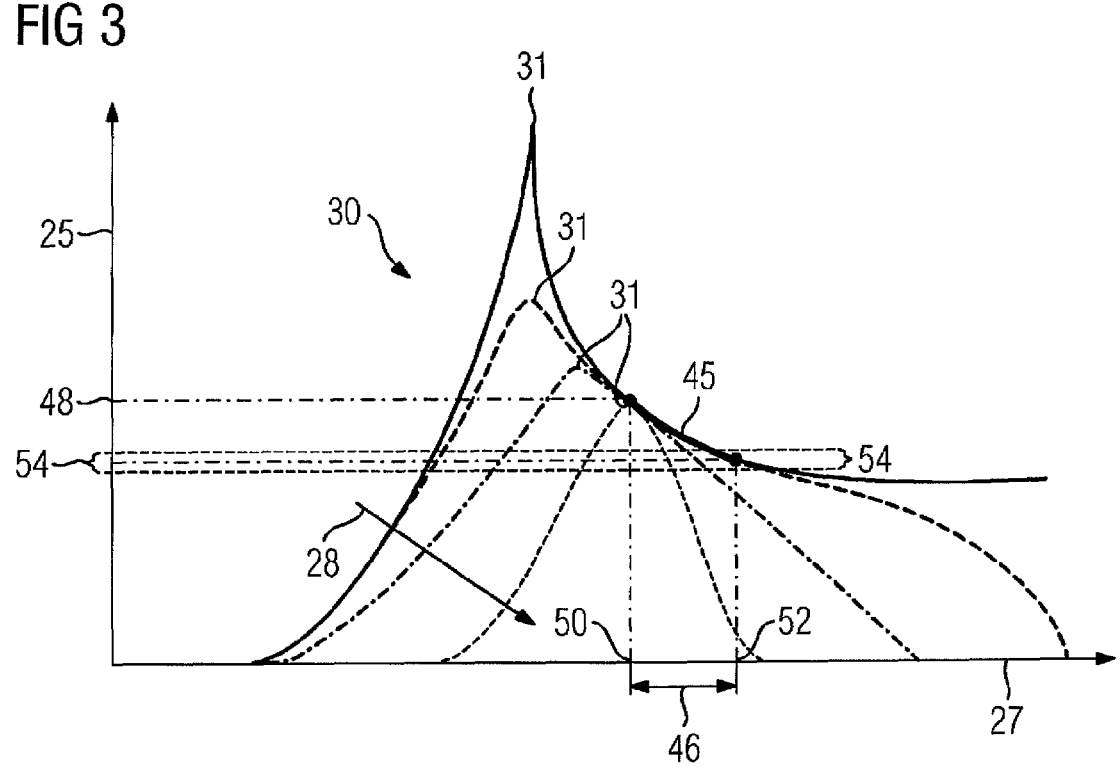
FIG. 3 depicts a diagram including the transmission characteristic of the circuit from FIGS. 1 and 2.

Reference is made to FIG. 1 and FIG. 3 that depict correspondingly a circuit diagram, an equivalent circuit and an attenuation diagram for a circuit 2 having a supply side 4 and a load side 6. The supply side 4 may be arranged, for example, on a stator of a computer tomograph and the load side 6 may be arranged on an annular tunnel of the computer tomograph.

So that the margin for movement of the annular tunnel is not unnecessarily restricted and the material wear of the elements for the transmission of energy from the supply side 4 to the load side 6 remains limited, the energy transmission is effected wirelessly via a transformer that is depicted as a real transformer 8 in FIG. 1. The real transformer 8 transmits a transmission voltage 9 from a primary winding 10 on the supply side 4 to a secondary winding 12 on the load side 6.

Figure 2:
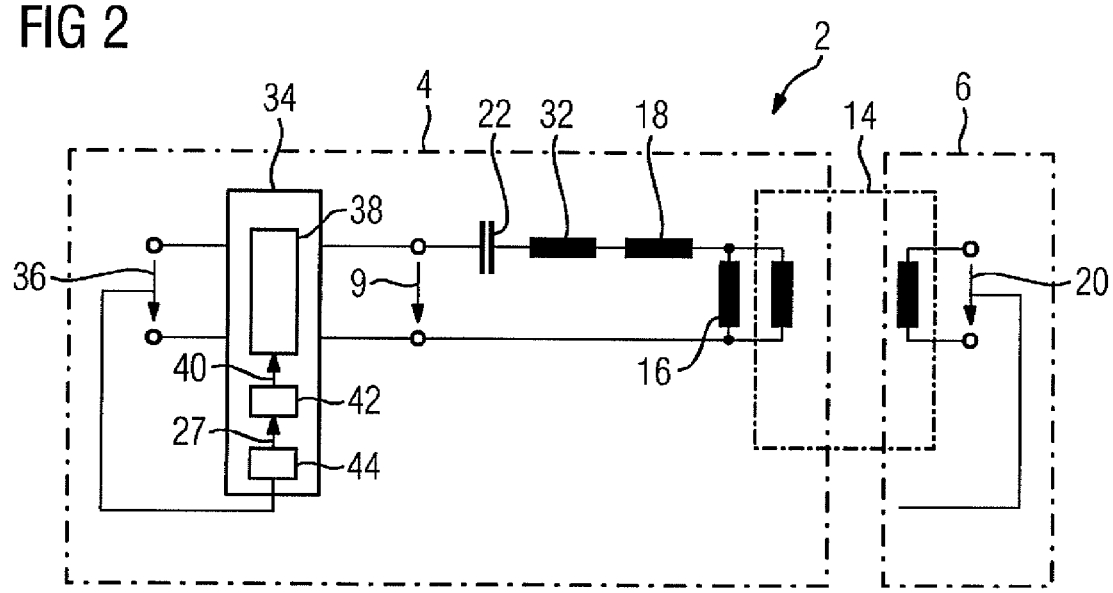
FIG. 2 depicts an equivalent circuit for the circuit diagram of FIG. 1.

As depicted in FIG. 2, the real transformer 8 may be replaced by a transformer 14 and its parasitic elements 16, 18 in an equivalent circuit. In the transformer 14, no energy losses occur during the transmission of the transmission voltage 9. The energy losses are represented by the parasitic elements 16, 18 of the real transformer 8 that include a main inductance 16 connected in parallel with the transformer 14 and a stray inductance 18 connected in series with the transformer 14 and are arranged on the supply side 4.

In this equivalent circuit, it is conventionally desired to dimension the main inductance 16 as large as possible since the equivalent circuit carries the magnetization current and to keep the stray inductance 18 as small as possible since its magnetic field does not contribute anything to the transmission and therefore interferes in the dimensioning. In contrast to this conventional approach, the embodiment uses the stray inductance 18 usefully, for example, in the modulation of an output voltage 20 of the circuit 2. The output voltage 20 is in this exemplary embodiment the load voltage that is dropped across the load on the load side. However, the output voltage 20 may still be reprocessed on the load side before the supply to the load in that, for example, the output voltage is rectified or filtered. For the subsequent explanations, the corresponding network components for rectification and/or for filtering may be assumed to be lossless for the sake of simplicity so that they will not be discussed further in the text which follows.

For the implementation of the present embodiment, a resonant circuit 24 is built up out of the primary winding 10 of the real transformer 8 and a capacitance 22, via which resonant circuit the transmission voltage 9 may be transmitted to the load side 6 by the real transformer 8. Since, as in FIG. 2, all parasitic elements 16, 18 of the real transformer 8 are arranged on the supply side 4 and no losses occur at the transformer 14, the resultant resonant circuit 24 dominates the transmission characteristic of the circuit 2 in the transmission of the transmission voltage 9. It is therefore possible to derive the output voltage 20 from the transmission voltage 9 and the transmission characteristic of the resonant circuit 24. Conversely, a desired output voltage 20 may be modulated via a suitable setting of the transmission voltage 9 without any intervention in a control system being necessary. An actual example of this control approach will be discussed in the text that follows.

The transmission characteristic of the resonant circuit 24 is described via control characteristics 30 that are depicted, by way of example, in FIG. 3. The control characteristics 30 plot the transmission ratio 25 of the circuit 2 over the frequency 27 of the transmission voltage 9. The transmission ratio 25 of the circuit 2 specifies the attenuation or amplification, respectively on the load side, of the transmission voltage 9 and may be calculated by the quotient of the transmission voltage 9 and the output voltage 20, taking into consideration the simplifications made above.

The appearance of the control characteristics 30 is influenced by the electrical load that is not depicted in FIGS. 1 and 2 on the load side 6. In FIG. 3, the influence of the load on the control characteristics 30 is indicated by an arrow 28. This influence 28 has great effects during starting and running-up of the load since the control characteristic 30 and thus the transmission characteristic of the circuit 2 change continuously in this phase.

In addition, the appearance of the control characteristics 30 may also be changed actively by the values of the capacitance 22. This primarily relates to the resonant frequencies 31 of the resonant circuit 24. If the available values of the capacitance 22 are not sufficient for matching the control characteristics to a desired transmission characteristic of the resonant circuit 24, an additional inductance 32 may also be accommodated optionally in the resonant circuit.

For the technical implementation of the control approach, described above, for modulating the output voltage 20, an actuating element 34 is provided that receives an input voltage 36 supplied to the supply side 4 and converts the input voltage into the transmission voltage 9. For the conversion, the actuating element 34 has an inverter 38, known to the expert, that adjusts the frequency 27 of the transmission voltage 9. For adjusting the frequency 27, the inverter 38 needs drive signals 40 that the inverter receives from a corresponding drive unit 42. For generating the drive signals 40, the drive unit 42 receives the frequency 27 that is to be adjusted in the transmission voltage 9 from an allocation unit 44 in which one of the control characteristics 30 of the resonant circuit 24, described above, may be stored.

In the operation of the previously described modulation of the output voltage 20, the allocation unit 44 may be initially initialized in that the allocation unit receives the input voltage 36, arbitrarily selects a starting frequency for the frequency 27 of the transmission voltage 9 and, on the basis of the allocation unit, determines the output voltage 20. If the inverter 38 outputs the transmission voltage 9 on the basis of this firmly predetermined frequency, this previously determined output voltage 20 occurs on the load side 6. If the input voltage 36 then changes, for example due to interfering influences, the allocation unit 24 may calculate, on the basis of the previously determined output voltage 20 and the now new input voltage 36, assuming that the inverter 38 is free of electrical losses, a necessary transmission ratio 25 in order to keep the output voltage 20 constant.

Since, due to the principle involved, the output voltage 20 is an alternating voltage, the alternating voltage is attempted by the drive to keep the output voltage 20 constant in its amplitude. But the output voltage 20 may also be a direct voltage, the transmission voltage 9 received at the secondary winding 12 being rectified before the direct voltage is output as output voltage 20. In this case, the level of the output voltage 20 is kept constant. For the sake of simplicity, however, the level of a direct voltage is to be designated as amplitude of a direct voltage.

On the basis of the necessary transmission ratio, the allocation unit may output the corresponding frequency 27 for the transmission voltage 9 to the inverter 38 in the control characteristic 30, so that the inverter adapts the transmission voltage 9 correspondingly in its frequency.

As already mentioned, the control characteristic 30 depends on a load connected on the load side 6, which is problematic in particular during the start-up of the load as the electrical power recorded, and thus the load, keeps on increasing. Although it is possible, in principle, to store all control characteristics 30 in the allocation unit, the selection of the correct control characteristic requires knowledge about the state of the load on the load side 6 and thus a feedback of information. However, this may be avoided, which is why a suitable control characteristic 45 is selected from the control characteristics depicted in FIG. 3. This suitable control characteristic 45 may then be load-independent over a particular frequency range 46. A method for determining this suitable control characteristic 45, which may be considered as being load-independent during the start-up of the load, will be described in the text that follows.

A fixed transmission ratio 48 of one, through which all control characteristics 30 run at a particular fixed frequency 50, is characteristic of all control characteristics 30. This fixed frequency 50 is therefore selected as lower limit frequency 50 for the frequency range 46. To determine the upper limit frequency 52 of the frequency range 46, a load range and a transmission ratio difference 54 may be predetermined. In the next act, the frequency 27 is determined in the diagram of FIG. 3 as the upper limit frequency 52 at which all control characteristics 30 still fall into the transmission ratio difference 54 for the predetermined load range. The load range may include, for example, the load states that occur until the load on the load side 6 has started a data transmission during start-up in order to send back information actively and start a corresponding control of the output voltage 20. From the control characteristics 30 for the predetermined load range, the suitable control characteristic may then be selected, interpolated or otherwise derived. This provides that in the frequency range 46, the suitable control characteristic 45 changes maximally with the transmission ratio difference 54 so that the suitable control characteristic 45 may be considered as constant in the range 46.

Figure 4:
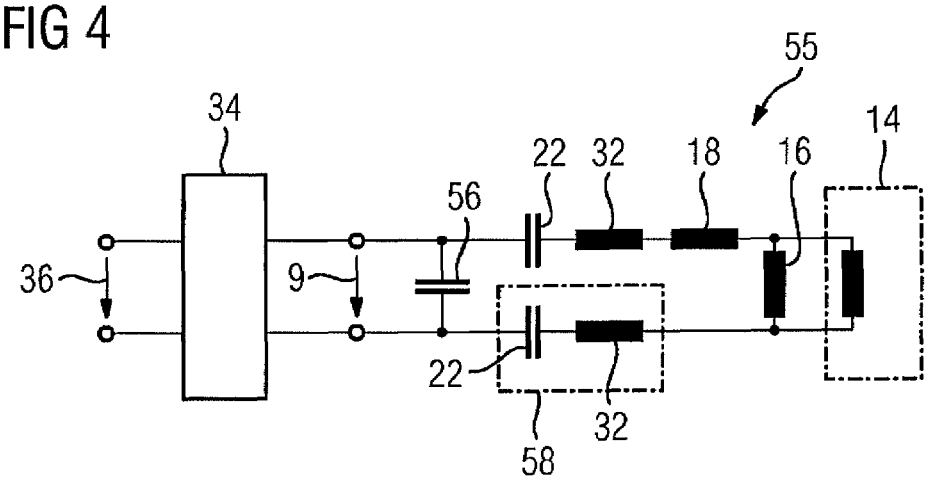
FIG. 4 depicts a circuit diagram of a second exemplary embodiment of the specified circuit.

FIG. 4 depicts a circuit diagram of the supply side 55 of the circuit according to a second exemplary embodiment. In FIG. 4, identical elements to FIGS. 1 to 3 are provided with the same reference symbols and will not be described again.

Compared with the first exemplary embodiment, the second exemplary embodiment is extended by a relief capacitance 56 and a symmetry resonant circuit 58.

The relief capacitance 56 short-circuits the transmission voltage 9 for high frequencies. As a result, highly transient components that lead to a rapid rise in the transmission voltage 9 are filtered out of the transmission voltage 9. This counteracts an unwanted radiation of interfering emissions by the resonant circuit 24. The relief capacitance 56 may either be selected in such a manner that the relief capacitance has no influence on the transmission characteristic 27 of the resonant circuit 24 or the relief capacitance may also be taken into consideration in the determination of the transmission characteristic of the resonant circuit 24.

As an alternative or additionally, a symmetry resonant circuit 58, in which the capacitance 22 and the additional inductance 32 are again arranged in series, may be arranged in the feedback branch of the supply side 55 of the circuit. Since the feedback branch of the supply side 55 of the circuit receives the transmission voltage 9 phase shifted by 180° compared with the resonant circuit 24, radiated interfering emissions are mutually cancelled by the resonant circuit 24 and the symmetry resonant circuit 58.

Figure 5:
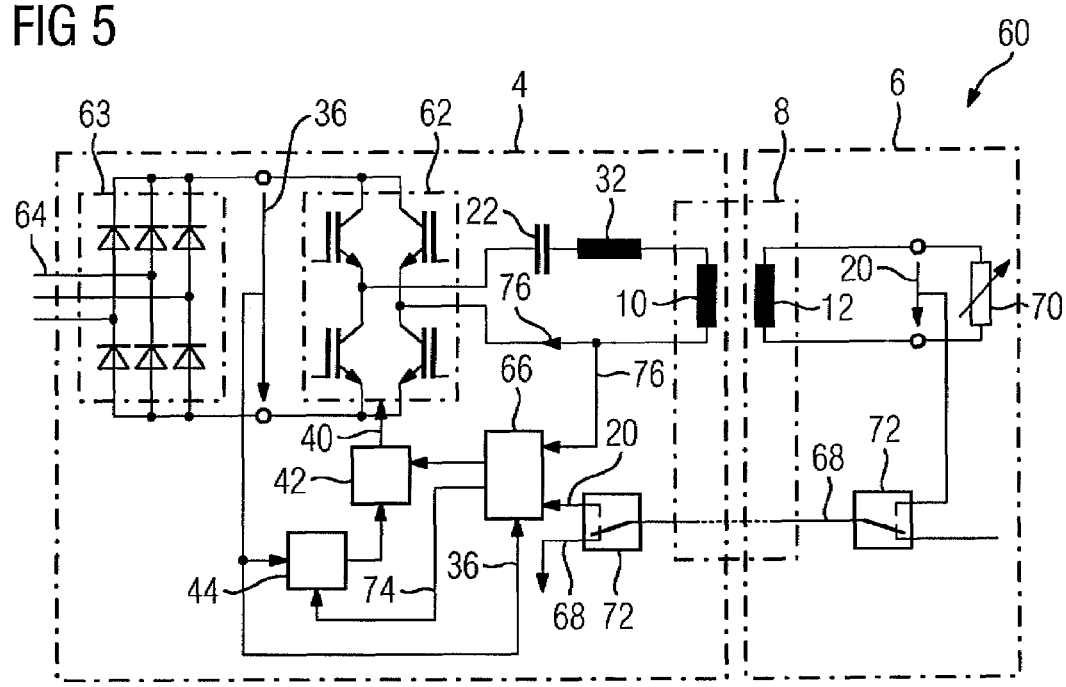
FIG. 5 depicts a circuit diagram of a third exemplary embodiment of the specified circuit.

FIG. 5 depicts a circuit diagram of a circuit 60 according to a third exemplary embodiment. In FIG. 5, elements identical to FIGS. 1 to 4 are provided with identical reference symbols and will not be described again. The third exemplary embodiment may be extended by the first and/or second exemplary embodiment.

In FIG. 5, the inverter 38 from FIGS. 1 and 2 is designed as inverter 62 and receives as input voltage 36 a three-phase voltage 64 rectified via a rectifier 63. In the exemplary embodiment in FIG. 5, a learning device 66 is provided that may utilize a data line 68 of the computer tomograph in order to feed the output voltage 20 present at the load 70 back into the supply side 4. For this purpose, both the supply side 4 and the load side 6 in each case has a multiplexer 72 so that the circuit 60 may utilize the data line 68 jointly with the sensors, not depicted in FIG. 5, of the computer tomograph.

The learning device 66 may be a processor that automatically measures an actual control characteristic of the resonant circuit 24 at a particular load state as suitable control characteristic 45. For this purpose, the load 70 may be put into a predefined state or disconnected completely from the load side 6.

For measuring the actual control characteristic, the learning device 66 may cause the inverter 62, for example via the drive unit 42, with suitable drive signals 40 to output a transmission voltage 9 with a sweep, in which the transmission voltage 9 moves once over all frequencies 27 of the frequency range 46 of the suitable control characteristic 45. The learning device 66 may thereupon detect the reaction of the output voltage 20 and the input voltage 36 and, using the resulting control characteristic data 74, update the suitable control characteristic 45 in the allocation unit 44.

As an alternative, the learning device 66 may also measure a current 76 through the primary winding 10 and, on the basis thereof, determine a phase difference between the transmission voltage 9 and the current 76. From this phase difference, the characteristic variables of the resonant circuit 24 may be derived directly.

Figure 6:
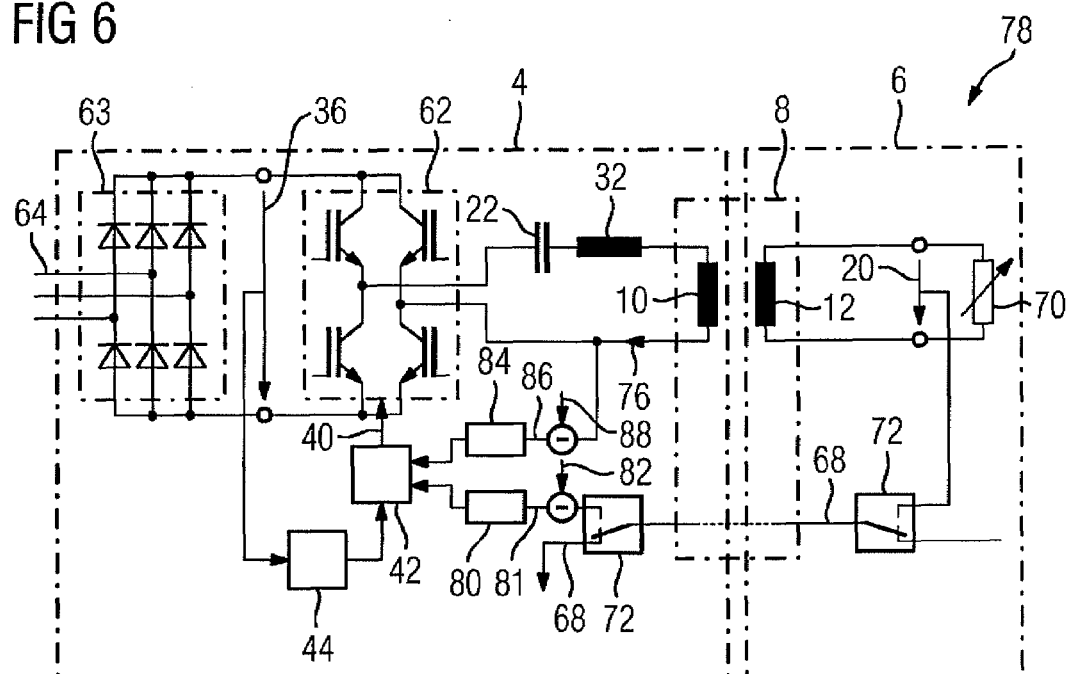
FIG. 6 depicts a circuit diagram of a fourth exemplary embodiment of the specified circuit.

FIG. 6 depicts a circuit diagram of a circuit 78 according to a fourth exemplary embodiment. In FIG. 6, elements identical to FIGS. 1 to 5 are provided with the same reference symbols and will not be described again. The fourth exemplary embodiment may be extended by one of the previous exemplary embodiments or a combination of them.

According to the fourth exemplary embodiment, the circuit 78 may have a voltage controller 80 that drives the drive unit 42 on the basis of a voltage control difference 81 between a nominal voltage 82 and the output voltage 20. The voltage controller may intervene when the data link 68 between the supply side 4 and the load side 6 has been built up. The control supports the voltage control in a particularly advantageous manner due to the fact that the voltage control moves the output voltage 20 very close to the nominal voltage 82. As a result, the control may settle rapidly to the nominal voltage 82.

In addition, a current controller 84 may also be provided that controls the drive unit 42 on the basis of a current control difference 86 between a nominal current value 88 and the current 76 through the primary winding 10. The nominal current value 88 may be a limit value for the current 76 through the primary winding 10 so that the components within the resonant circuit 24 are protected against too high a current and therefore against an electrical overload.

Overall, the transmission characteristic of a resonant circuit constructed of the primary winding of a real transformer and a capacitance connected thereto is thus utilized for controlling the output voltage of the transformer.

Although the embodiments have been illustrated and described herein, the embodiments are not restricted by the examples disclosed and other variations may be derived therefrom by the expert without departing from the protective scope of the embodiments.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A circuit for transmitting an input voltage from an electrical energy source in a stator to a load within a device movable relative to the stator, the circuit comprising:
   an actuating element configured to convert an input voltage into a transmission voltage;
   a resonant circuit configured to receive the transmission voltage, wherein the resonant circuit includes a capacitance and a primary winding of a transformer; and a memory configured to store a plurality of control characteristic values based on a measurement of transmission ratios of the resonant circuit, wherein the transformer comprises the primary winding and a secondary winding, wherein the primary winding is configured to transmit the transmission voltage to the secondary winding and the secondary winding is configured to deliver the received transmission voltage as an output voltage to the load, and wherein the actuating element is configured to adjust the frequency of the transmission voltage based on the plurality of control characteristic values such that the transmission ratio of the resonant circuit remains essentially constant between the transmission voltage and the output voltage for a predetermined load range of the load.

2. The circuit of claim 1, wherein the actuating element is configured for adjusting the frequency of the transmission voltage on the basis of a control characteristic in which the transmission ratio of the resonant circuit is plotted over the frequency to be adjusted.

3. The circuit of claim 2, wherein a shape of the control characteristic remains essentially constant within the predetermined load range.

4. The circuit of claim 2, further comprising a device configured to detect an input voltage of the actuating element, wherein the actuating element is configured for adjusting the frequency of the transmission voltage on the basis of the control characteristic such that the output voltage is independent of the input voltage.

5. The circuit of claim 1, wherein the capacitance is connected in series with the primary winding, and the circuit has a relief capacitance that is connected in parallel with the primary winding.

6. The circuit of claim 1, wherein the actuating element is configured to adjust the frequency within a predetermined frequency range.

7. The circuit of claim 6, wherein the capacitance is selected such that the resonant frequency of the resonant circuit is outside the frequency range.

8. The circuit of claim 6, wherein the frequency range is selected such that the control characteristic comprises a fixed frequency in which the transmission ratio is independent of an impedance of the load.

9. The circuit of claim 8, wherein the limit frequency of the frequency range is the fixed frequency toward the resonant frequency.

10. The circuit of claim 9, wherein the other limit frequency of the frequency range is selected from a second frequency range in which the transmission ratio changes load-dependently within a transmission ratio range.

11. The circuit of claim 10, wherein the predetermined range states comprises load states during start-up of a load, connected to the circuit, in the movable device.

12. The circuit of claim 1, wherein the write device is configured to measure the transmission ratio on the basis of a step response.

13. The circuit of claim 12, wherein the write device for measuring the transmission ratio is configured to measure the zero transitions of the step response.

14. The circuit of claim 1, wherein the write device is configured to measure the transmission ratio at at least one point of the control characteristic and to correct the control characteristic on the basis of the at least one measured point.

15. The circuit of claim 1, wherein the write device is configured to measure the transmission ratio on the basis of a sweep of the frequency of the transmission voltage.

16. The circuit of claim 15, wherein the circuit is configured to connect the resonant circuit directly to an output of the circuit during the sweep.

17. The circuit of claim 1 further comprising a write device configured to store values of the control characteristic in the memory on the basis of a measurement of the phase difference between the transmission voltage and the current through the primary winding.

18. The circuit of claim 17, further comprising a connection of interfering variables of the input voltage via the control characteristic for faster correction of the load voltage.

19. The circuit of claim 1 further comprising a current measuring device configured to measure a resonant circuit current through the resonant circuit, wherein the actuating element is configured to control the frequency of the transmission voltage such that the current through the resonant circuit does not exceed a predetermined value.

20. The circuit of claim 1 further comprising a voltage measuring device for measuring the load voltage, wherein the actuating element is configured for controlling the load voltage on the basis of the frequency of the transmission voltage such that the load voltage follows a nominal voltage value.

21. The circuit of claim 20, wherein the voltage measuring device is arranged on the stator side and includes a data receiving device configured to receive the load voltage from the movable device.

22. The circuit of claim 21, wherein the circuit is configured to start the control of the load voltage on the basis of the frequency when the load voltage is available at the data receiving device.

23. The circuit of claim 22, wherein the circuit is configured to end the adjustment of the frequency of the transmission voltage on the basis of the control characteristic when the control of the load voltage has been started.

24. The circuit of claim 22, wherein the capacitance, the additional inductance, and the primary winding are connected in series.

25. The circuit of claim 1 comprising an additional inductance at the transformer that is connected in series with the primary winding.

26. The circuit of claim 25 further comprising a further resonant circuit symmetric to the resonant circuit, the further resonant circuit having a series circuit of a symmetry capacitance corresponding to the capacitance and a symmetry inductance corresponding to the additional inductance, wherein the primary winding is connected between the resonant circuit and the further resonant circuit.

27. A method for transmitting an input voltage from an electrical energy source in a stator to a load within a device movable relative to the stator, the method comprising:

converting the input voltage into a transmission voltage;

receiving the transmission voltage with a resonant circuit that contains a capacitance and a primary winding of a transformer;

transmitting the transmission voltage to a secondary winding of the resonant circuit;

delivering the transmission voltage received by the secondary winding to the load;

measuring and storing, in a memory, a control characteristics of the resonant circuit based on a transmission ratio of the resonant circuit; and adjusting the frequency of the transmission voltage based on the plurality of control characteristics including the control characteristic stored in the memory, such that the transmission ratio of the resonant circuit remains essentially constant for a predetermined range of values of a load which can be connected to the secondary winding so that the transmission ratio of the resonant circuit is independent of the load within the predetermined range of values.

28. A tomograph for recording a spatial structure of an object, the tomograph comprising:
an annular tunnel configured to rotate around a stator during the recording; and
a load located within the annular tunnel;
wherein the stator comprises:
an electrical energy source;
an actuating element configured to convert an input voltage into a transmission voltage,
a resonant circuit configured to receive the transmission voltage, wherein the resonant circuit contains a capacitance and a primary winding of a transformer,
a memory configured to store a plurality of control characteristic values based on a measurement of transmission ratios of the resonant circuit; and
wherein the transformer comprises the primary winding and a secondary winding, wherein the primary winding is configured to transmit the transmission voltage to the secondary winding and the secondary winding is configured to deliver the received transmission voltage as an output voltage to the load,
wherein the actuating element is configured to adjust the frequency of the transmission voltage based on the plurality of control characteristic values in such a manner that the transmission ratio of the resonant circuit remains essentially constant between the transmission voltage and the output voltage for a predetermined load range of the load.

* * * * *